United States Patent [19]

Himeno et al.

[11] Patent Number: 5,296,383
[45] Date of Patent: Mar. 22, 1994

[54] HUMAN CENTROMERE ANTIGEN POLYPEPTIDE

[75] Inventors: Michio Himeno; Kenji Sugimoto, both of Sakai, Japan

[73] Assignee: Daikin Industries, Ltd., Osaka, Japan

[21] Appl. No.: 879,685

[22] Filed: May 7, 1992

[30] Foreign Application Priority Data

May 8, 1991 [JP] Japan .................. 3-102517

[51] Int. Cl.$^5$ .......................... G01N 33/564
[52] U.S. Cl. ...................... 436/507; 436/506; 530/300; 435/7.1
[58] Field of Search ............ 530/324, 300; 435/5, 435/7.1; 436/506–508

[56] References Cited

PUBLICATIONS

Earnshaw et al: Analysis of anticentromere ... CENP-B PNAS vol. 84 pp. 4979–4983 Jul. 1987.
Sullivan, K. F. et al., "CENP-B is a highly conserved mammalian centromere protein with homology to the helix–loop–helix family of proteins" Chromosoma (1991) 100:360–370.
Earnshaw et al., J. Cell Biol. (1987) 104:817–829.
Earnshaw et al., Proc. Natl. Acad. Sci. (1987) 84:4979–4983.
Rothfield et al., Arthritis and Rheumatism (1987) 30(12):1416–1419.

Primary Examiner—Christine M. Nucker
Assistant Examiner—Jeffrey Stucker
Attorney, Agent, or Firm—Morrison & Foerster

[57] ABSTRACT

The present invention provides polypeptides composing epitopes of human centromere protein B, genes encoding therefor, plasmids or phages containing the genes, transformants obtained by introducing the plasmids or phages containing the genes, a method for producing the human centromere antigen polypeptide using the transformant, and a method for detecting anti-centromere antibody using the human centromere antigen polypeptide. Analysis of the above-mentioned epitope was accomplished using CENP-B gene obtained from a cDNA library prepared using mRNAs isolated from Jurkat cells. The present invention allows the production of the human centromere protein B epitope region in a large quantity, which in turn allows the detection of human anti-centromere antibody readily and precisely using the peptide obtained. Furthermore, it becomes possible to make a precise classification of the disease type of a patient having human anti-centromere antibody by determinations using each of the epitopes.

2 Claims, 10 Drawing Sheets

FIG. 4A

```
433
GAA GGA GAG GAA TTG GGG GAG GAA GAG GAG GTG GAG GAG GGT GAT GTT GAT ACT GAT
Glu Gly Glu Glu Leu Gly Glu Glu Glu Glu Val Glu Glu Gly Asp Val Asp Ser Asp
                440                 450

GAA GAG GAG GAT GAG GAG AGC TCC TCG GAG GGC TTG GAG GCT GAG GAC TGG GCC
Glu Glu Glu Asp Glu Glu Ser Ser Ser Glu Gly Leu Glu Ala Glu Asp Trp Ala
        460                 470                 480

CAG GGA GTA GTG GAG GCC GGT GGC AGC TTC GGG GCT TAT GGT GCC CAG GAG GAA GCC CAG
Gln Gly Val Val Glu Ala Gly Gly Ser Phe Gly Ala Tyr Gly Ala Gln Glu Ala Gln
        490                 500                 510

TGC CCT ACT CTG CAT TTC CTG GAA GGT GGG GAG GAC TCT GAT TCA GAC AGT GAG GAA GAG
Cys Pro Thr Leu His Phe Leu Glu Gly Gly Glu Asp Ser Asp Ser Asp Ser Glu Glu Glu
```

```
                                                    520                           530
GAC GAT GAG GAA GAG GAT GAT GAA GAC GAC GAT GAT GAG GAG GAT GGT GAT
Asp Asp Glu Glu Glu Asp Asp Glu Asp Asp Asp Asp Glu Glu Asp Gly Asp 540                           550
GAG GTG CCT GTA CCC AGC TTT GGG GAG GCC ATG GCT TAC TTT GCC ATG GTC TAC AAG AGG TAC
Glu Val Pro Val Pro Ser Phe Gly Glu Ala Met Ala Tyr Phe Ala Met Val Lys Arg Tyr 560                           570
CTG ACC TCC TTC CCC ATT GAT GAC CGC GTG CAG AGC CAC ATC CTC CAC TTG GAA CAC GAT
Leu Thr Ser Phe Pro Ile Asp Asp Arg Val Gln Ser His Ile Leu His Leu Glu His Asp 580                           590
CTG GTT CAT GTG ACC AGG AAG AAC CAC GCC AGG CAG GCG GGA GTT CGA GGT CTT GGA CAT
Leu Val His Val Thr Arg Lys Asn His Ala Arg Gln Ala Gly Val Arg Gly Leu Gly His

504
CAA AGC TGA
Gln Ser
```

FIG. 4B

| | REACTIVITY WITH PATIENT'S SERA (GROUP I) |
|---|---|
| pB-2-6  | + |
| pB-1-1  | — |
| pB-2-16 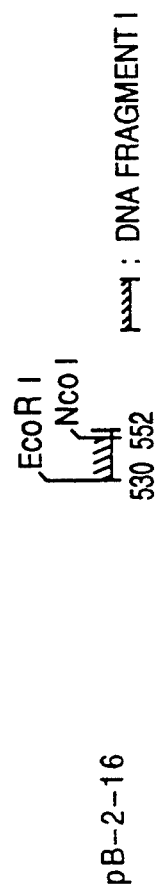 | — |
〰〰 : DNA FRAGMENT I
FIG. 6B

```
                    530                                    540
         AspGlyAspGluValProValProSerPheGlyGluAlaMetAlaTyrPheAlaMet
5'-AATTCAGATGGTGATGAGGTGCCTGTACCCAGCTTTGGGGAGGCCATGGCTTACTTTGC-3'
3'-    GTCTACCACTACTCCACGGACATGGGTCGAAACCCCTCCGGTACCGAATGAAACGGTAC-5'
```

FIG. 7

HUMAN CENTROMERE ANTIGEN POLYPEPTIDE

BACKGROUND OF THE INVENTION

1. Field of the Invention

This invention relates to a polypeptide containing at least a specific antigenic region of a human centromere antigen recognized by a human anti-centromere antibody, a gene encoding the polypeptide, a plasmid or a phage containing the gene, a transformant obtained by transforming a host with the plasmid or the phage, a method for producing the human centromere antigen polypeptide utilizing the transformant and a method for detecting an anti-centromere antibody using the human centromere antigen polypeptide.

2. Description of the Prior Art

Autoimmune diseases are among the nationally designated incurable diseases in Japan, and it is required to elucidate causes of the diseases and develop therapeutic methods. Various antibodies against various own cellular components (autoantibodies) are present in the serum of an autoimmune disease patient. It is thought there is an association of these autoantibodies with the diseases.

An anti-centromere antibody is one of the antinuclear antibodies present in the central region of a mitotic cell chromosome and reacts with a protein of "a centromere domain" which plays an important role in the separation of a chromosome in a mitotic phase. An anti-centromere antibody has been pointed out as an autoantibody related to some autoimmune diseases, particularly scleroderma. Scleroderma is a general name for the disease inclusive of various disease types, and a method of clinical assay for an easier and more precise classification of the disease type is required to be established in order to diagnose and treat the disease.

An indirect fluorescent antibody technique is currently employed for detecting an anti-centromere antibody in a patient's serum using a liver section or cultured cells as nuclear materials. In order to strictly distinguish the positive antibody from other antibodies present in the serum in the indirect fluorescent antibody method, it should be further confirmed that the anti-centromere antibody recognizes the centromere region on a chromosome further utilizing a chromosome smear of cells in a mitotic phase. The method has disadvantages in that it requires a chromosome smear preparation and a specific facility and labors for microscopic observation of the smear, so that it is not suitable for a clinical assay handling a large number of people. For an alternative method for detecting the anti-centromere antibody activity, a method using a chromosomal centromere region as an antigen prepared from human cells in large quantity is assumed, but it is still too costly and labor intensive for practical use.

Presence of human centromere antigens, each of them including centromere protein A, B or C of different molecular weight has been identified. Among them, the major antigen is human centromere protein B (CENP-B), a portion of the gene coding for the protein has been cloned [Earnshaw, W. C., et al., J. Cell Biol., 104: 817 (1987)]. However, the epitopes contained in CENP-B have not been analyzed in detail yet. For the precise detection and classification of an anti-centromere antibody, detailed analysis of epitopes of the major antigen CENP-B is desired.

In order to solve the conventional problems described above and to develop a method for measuring anti-centromere antibody specifically as well as readily, elucidation of the epitopes of the major human centromere antigen, human centromere protein B and the production of the polypeptides corresponding to each epitope in a large quantity are desired.

SUMMARY OF THE INVENTION

The polypeptide containing a human centromere protein B epitope of the present invention is a polypeptide selected from the group consisting of polypeptide I and polypeptide II having the following amino acid sequences shown by SEQ ID NO:1 and SEQ ID NO:2, and a polypeptide having a portion thereof.

| Polypeptide I (shown in SEQ ID NO:1) |
|---|
| Asp Gly Asp Glu Val Pro Val Pro Ser Phe Gly Glu Ala Met |
| Ala Tyr Phe Ala Met Val Lys Arg Tyr Leu Thr Ser Phe Pro |
| Ile Asp Asp Arg Val Gln Ser His Ile Leu His Leu Glu His |
| Asp Leu Val His Val Thr Arg Lys Asn His Ala Arg Gln Ala |
| Gly Val Arg Gly Leu Gly His Gln Ser |
| Polypeptide II (shown in SEQ ID NO:2) |
| Ser Ser Glu Gly Leu Glu Ala Glu Asp Trp Ala Gln Gly Val |
| Val Glu Ala Gly Gly Ser Phe Gly Ala Tyr Gly Ala |

The present invention comprises a gene encoding the above mentioned polypeptide containing a human centromere protein B.

The present invention comprises a plasmid or phage vector containing the above-mentioned gene.

The present invention comprises a host cell transformed with the above-mentioned plasmid or phage vector.

The method of the present invention for producing the polypeptide containing a human centromere protein B described above comprises the steps of culturing the host cell transformed with the plasmid or phage vector containing the gene described above, and isolating and purifying the polypeptide from the culture.

The method of the present invention for detecting a human anti-centromere antibody comprises the following steps of:

(a) adding the above-mentioned polypeptide to a sample to contact the polypeptide with a human anti-centromere antibody contained in the sample; and (b) detecting the human anti-centromere antibody bound to the polypeptide.

Thus, the invention described herein, makes possible the objectives of (1) providing a polypeptide containing an epitope of human centromere protein B epitopes; (2) providing a method for producing the polypeptide on a large scale by the use of a recombinant technique; and (3) providing a method for detecting the anti-centromere antibody employing the polypeptide.

BRIEF DESCRIPTION OF THE DRAWINGS

This invention may be better understood and its numerous objects and advantages will become apparent to those skilled in the art by reference to the accompanying drawings as follows:

FIGS. 4a and b show the complete nucleotide sequence for the coding region of the CENP-B gene fragment inserted in pCENP-B-1 and the corresponding amino acid sequence.

FIG. 7 shows the nucleotide sequence of the DNA fragment I used for the preparation of pB-2-6, pB-1-1 and pB-2-16, and the corresponding amino acid sequence.

DESCRIPTION OF THE PREFERRED EMBODIMENTS

The inventors of this invention constructed a cDNA library using messenger RNAs (mRNAs) extracted from human T cell-derived human Jurkat cells to clone human centromere protein B gene, CENP-B gene. CENP-B gene was isolated from the library, from which deletion mutant genes were prepared. Then, the reactivity of the deletion mutant gene product and a patient serum containing anti-centromere antibody was analyzed to determine regions for major epitope I and II. Accordingly, the present invention was completed.

The gene coding for CENP-B of this invention can be obtained as follows. First, mRNAs are isolated from human derived tissues, cells, and cell lines, preferably from human T cell-derived Jurkat cells to construct a cDNA library. A cDNA library can be constructed according to an appropriate technique known in the art, such as the method described by Young et al. employing a Lambda gt11 phage vector [Young, R. A., et al., *Proc. Natl. Acad. Sci. USA.*, 80: 194 (1983)]. The cDNA library so obtained (e.g. the library utilizing *E. coli*) can be screened for a clone expressing human centromere antigen by using anti-centromere antibody, i.e. by examining whether proteins expressed by the constructed cDNA library react with the anti-centromere antibody. In the expression of human centromere antigen described above, human centromere antigen itself can be expressed, while it can be expressed as a fusion protein of human centromere antigen and another protein, preferably as a fusion protein with *E. coli* β-galactosidase. In this case, the β-galactosidase activity can be used as an indicator.

Figure 1:
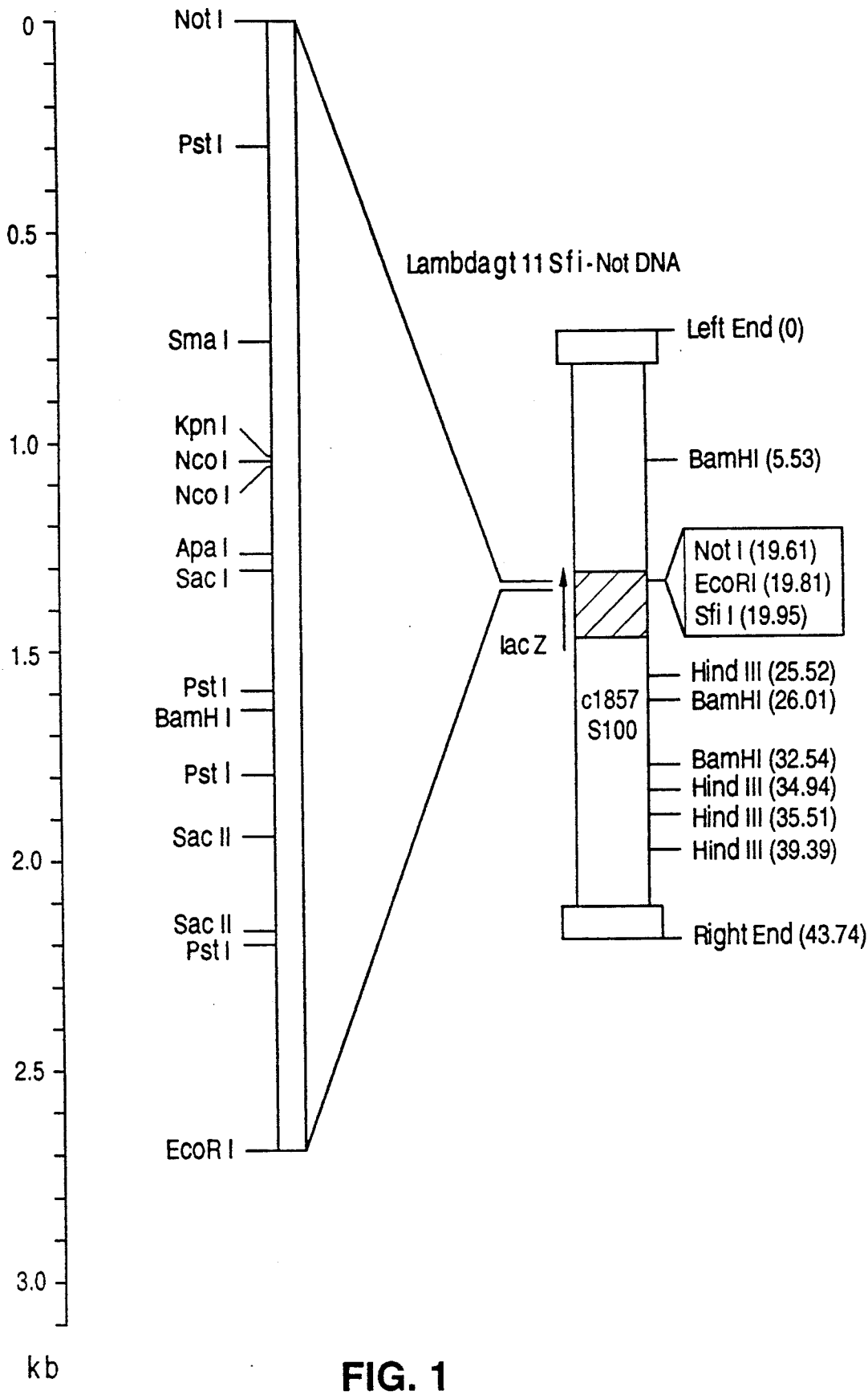
FIG. 1 illustrates the restriction map of Lambda gt11 Sfi-Not vector DNA (upper) and the longest fragment (lower) containing a CENP-B gene which had been inserted in the vector DNA.
Figure 2:
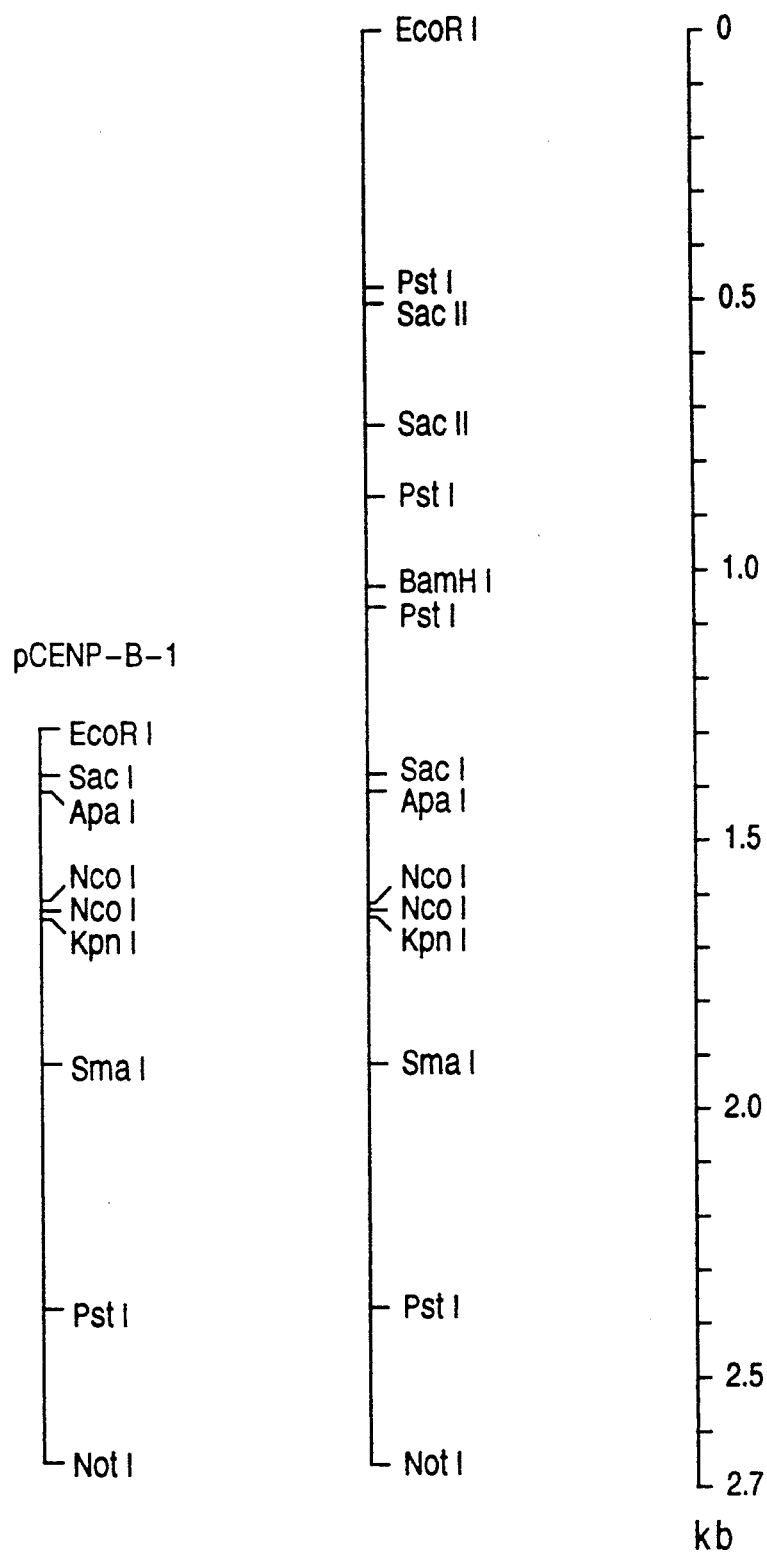
FIG. 2 illustrates the restriction maps of the longest fragment (the same fragment as in FIG. 1) and the shortest fragment (the inserted DNA fragment contained in pCENP-B-1) among the inserted DNA fragments containing CENP-B gene.

Then, a phage DNA is isolated from the positive clones (*E. coli*) screened as described above. By restriction enzyme analysis of this DNA, the insertion of the cDNA of interest into the phage DNA can be confirmed and a restriction map can be prepared. The gene coding for human centromere protein B is selected from these clones positive for human centromere proteins obtained as described above, and cloned. This is performed by, for example, the method of selecting the clone which exhibits a restriction map similar to that of the CENP-B gene cloned by Earnshaw, et al. The restriction map of the longest fragment among the resultant DNA fragments containing human centromere gene, and the restriction map of the Lambda gt11 Sfi-Not vector DNA containing the fragment are shown in FIG. 1. In addition, the restriction maps of the longest fragment (supra) and the shortest fragment among the DNA fragments containing human centromere antigen gene are shown in FIG. 2.

Furthermore, an epitope of the CENP-B gene obtained as described above is determined. The determination of a CENP-B gene epitope is performed as follows. Various deletion mutant genes are prepared from the gene by using various restriction enzymes, exonuclease and the like, and then the determination can be performed by analyzing the reactivities of the polypeptides produced by the deletion mutant genes and the patient sera containing anti-centromere antibody. Practically, the determination is made by the following method. First, CENP-B gene fragments with various length having a deletion at 3' end of the nucleotide (shown in FIG. 3) are prepared. The method for preparing a gene fragment associated with such a deletion mutation is described in "Zoku Seikagaku Jikken Kouza, Vol. 1, 'Methods for Studying Genes II' pp. 289–305, the Japanese Biochemical Society ed.". The results shown in FIG. 3 were obtained by the examination of the interactions between the polypeptides expressed by the above-described expression vectors (the names of the vectors are shown at the left end of FIG. 3) and the patient sera containing anti-centromere antibody by Western blot. Among the polypeptides having the reactivity with the patient sera, some polypeptides reacted with 40 serum samples out of the 40 serum samples while others reacted with only 11 serum samples out of the 40 serum samples, which indicates that the CENP-B antigen polypeptide coded by pCENP-B-1 (the preparation method of which is described in Example I.1-4) possesses a plural number of epitopes.

Then, the fragments shown in FIG. 5 were prepared, and the polypeptides were expressed and reacted with the sera containing anti-centromere antibody in the same way as described above, the results of which are shown in FIG. 5. This reveals that one of the CENP-B epitopes is within the amino acid sequence coded by the DNA fragment contained in pS-1-35 shown in FIG. 5, e.g. within the amino acid sequence from 462 to 487 (the amino acid numbers correspond to those of the sequence described by Earnshow, W. C., et al., *J. Cell Biol.*, 104: 817 (1987); the amino acid sequence is shown in SEQ ID NO:2). The amino acid sequence supra is designated as polypeptide II. Furthermore, the fragments shown in FIG. 6 were prepared, and the polypeptides were expressed and reacted with the sera containing anti-centromere antibody as the same way as described above, the results of which are shown in FIG. 6. This reveals that one of the CENP-B epitopes is within the amino acid sequence coded by the DNA fragment contained in pB-2-6 shown in FIG. 6, e.g. within the amino acid sequence from 530 to 594 (the amino acids are numbered the same as described above; the amino acid sequence is shown in SEQ ID NO:1). The amino acid sequence above is designated as polypeptide I. Accordingly, one of the CENP-B epitopes is contained in the sequence consisting of 26 amino acids from 462 to 487 of the polypeptide and the other in the sequence consisting of 65 amino acids from 530 to 594 of the polypeptide. The present invention comprises the polypeptides containing these epitopes. It is possible to produce the polypeptides by microorganism such as *E. coli* or yeast, or by animal cells or the like using the genes encoding the polypeptides, i.e. an appropriate promoter region may be linked to the 5' end of the each gene encoding each polypeptide obtained above, which is then inserted into a suitable plasmid followed by introducing them into a microorganism such as *E. coli* or yeast or animal cells to culture. The polypeptide corresponding to each epitope can be expressed as itself, while it can be expressed as a fusion protein with other protein, preferably with *E. coli* βgalactosidase or bacteriophage T7 gene 10 protein [Studier, F., et al., *J. Mol. Biol.*, 189: 113 (1986)]. These manipulations can be made using known techniques in the art. Each polypeptide can be isolated and purified by column chromatography or by an immunochemical method also known in the art.

Alternatively, these polypeptides can be synthesized by the conventional methods of liquid phase or solid phase peptide synthesis or enzymatic synthesis ("Zoku Seikagaku Jikken Kouza" Vol. 2, 'Protein Chemistry, No. 2', page 663, 1987).

The resultant polypeptides containing each of the epitopes are used for the determination of the anti-centromere antibody activity. The methods for the determination include conventional immunological assays such as RIA, ELISA, Western blot and the like. The process of reaction (solid phase or liquid phase), labeling, detection and the like are not limited. The samples include, but are not limited to, urine, saliva, blood, serum, tissue and feces.

When the patient sera diagnosed as positive by the conventional indirect immunofluorescence assay are determined using polypeptide I or polypeptide II of this invention, the sera are divided into those which only react with polypeptide I and others which react with the both polypeptides I and II. As described above, the patients with anti-centromere antibody can be subdivided by the recognition of the each epitope (i.e. by the reactivity with polypeptide I or II), and the subdivision may be an important indicator for a precise classification of the disease type for a patient with anti-centromere antibody.

EXAMPLES

In order that this invention may be better understood, the following examples are set forth.

EXAMPLE I

1. Extraction of Total RNAs

Jurkat cells were cultured in RPMI 1640 medium supplemented with 10% fetal calf serum, and the total RNA was extracted from these Jurkat cells by the conventional method using guanidinium thiocyanate (GuSCN) as follows [Chirgwin, J. M., et al., *Biochemistry*, 18: 5294 (1979)]. First, Jurkat cells (about $5 \times 10^7$ cells) were suspended in a guanidinium thiocyanate/lithium chloride solution (0.5 g of GuSCN was dissolved into 0.58 ml of 25% lithium chloride solution, then 20 μl of 2-mercaptoethanol was added thereto) and sheared by a syringe until the viscosity lowered. After that, the solution was layered on a 5.7M cesium chloride solution, then centrifuged for separation. The total RNA peletted at the bottom of the centrifuge tube was dissolved in RNAse-free water, and then recovered by ethanol precipitation. 2. Preparation of Messenger RNA The messenger RNAs were prepared from the total RNA obtained in section 1 using an oligo dT cellulose column type 3 (Collaborative Research, Co.) as follows. First, the above-mentioned column was washed with TE buffer (10 mM Tris-HCl, 1 mM EDTA, pH 7.5), then equilibrated with a TE/NaCl solution (1:1 mixture of TE buffer and 1M NaCl solution). The precipitate of the total RNA obtained in section 1 was dissolved in TE buffer, kept at 65° C. for five minutes, and cooled down immediately. After an equal volume of 1M NaCl solution was added, the mRNA solution was loaded on the column. The column was washed with five bed volumes of the TE/NaCl solution, then mRNAs were eluted with three bed volumes of TE buffer. After the NaCl concentration of the mRNA eluate was adjusted to 0.5M, the eluate was subjected to the column for rechromatography to purify the mRNAs. The resultant purified mRNA fractions were pooled, ethanol-precipitated, and then dissolved into TE buffer.

3. Construction of a cDNA Library Using Lambda gt11 Vector cDNAs were synthesized using 4 μg of the mRNA obtained in section 2 and 1.8 pg of Not I primer adapter (Promega Co.) [Han, J. H., et al., *Biochemistry*, 26: 1617 (1987); Gubler, U., et al., *Gene*, 25: 263 (1983)]. To the resultant cDNA, a EcoRI adapter was ligated using a RiboClone EcoRI Adapter-Ligation System (Promega Co.). 5'-OH of the EcoRI adapter was phosphorylated by T4 polynucleotide kinase upon digestion with Not I restriction enzyme. These cDNAs were separated by 1% agarose gel electrophoresis, and the cDNAs with sizes ranging from about 1.2 kb to about 7 kb were isolated. The resultant cDNAs were inserted into Lambda gt11 Sfi-Not vectors (Promega Co.) which had been double-digested with EcoRI and NotI restriction enzymes, then packaged into phage particles using a GIGAPACKII (StrateGene Co.) to obtain a cDNA library.

4. Separation of Positive Clones by Screening with Antibody and Analysis of the Clones Patient sera diagnosed as positive for anti-centromere antibody by indirect immunofluorescence were used for the screening. The indirect immunofluorescence was performed according to the conventional technique [Motoki, *Nihon Rinsho*, 48: pp. 580–583 (1990 Suppl.)].

The screening with an antibody was performed by the following method using an Express Blot Assay Kit (BioRad Co.).

*E. coli* Y1090 was infected with the phage particles obtained in section 3 for plaque formation. The nitrocellulose filter, which was soaked into 10 mM IPTG and air-dried, was placed on the plate having about 500,000 to 600,000 phage plaques produced (about 20,000 plaques per dish) and the plate was incubated at 37° C. for two hours to induce the gene products of the inserted cDNAs (i.e. fusion proteins with β-galactosidase), so that the gene products were transferred onto the filter. After cooling at 4° C. for 10 minutes, the filter was removed from the plate and treated in a blocking solution (3% gelatin, 20 mM Tris-HCl, pH 7.6, 0.5M NaCl) at a room temperature for one hour, then washed with a TBS solution (20 mM Tris-HCl, pH 7.6, 0.5M NaCl). The above-mentioned human anti-centromere antiserum was diluted about 10,000 fold with an antibody diluting solution (1% gelatin, 20 mM Tris-HCl, pH 7.6, 0.5M NaCl, 0.05% Tween 20), and then the diluted serum was reacted with the gene product on the filter at 4° C. overnight with shaking. The filter was washed with a T-TBS solution (a TBS solution containing 0.05% Tween 20) three times, then soaked in a diluted alkaline phosphatase-conjugated goat anti-human antibody solution (BioRad Co.), which was diluted 3000 fold with the antibody diluting solution, with shaking at room temperature for several hours. After the filter was washed subsequently with a T-TBS solution once and a TBS solution twice, a BCIP.NBT (BioRad Co.) substrate solution for alkaline phosphatase was added to develop color.

The rescreening of the positive clones which developed the color by the procedure described above was performed by the same procedure as described above using human anti-centromere antiserum. As the result, 13 clones which reproducibly reacted with human centromere antibody were obtained. These clones were designated as clones Lambda gt11 CENP-1, 2, 3, 4, 5, 6, 7, 8, 9, 10, 11, 12 and 13, respectively.

Phage DNAs were isolated from these 13 clones according to the standard method. After the phage DNA was double-digested with restriction enzymes EcoRI and NotI, the DNA was separated by 1% agarose gel electrophoresis for size determination of the inserted fragments.

One of 13 clones, Lambda gt11 CENP-1 was selected, and its inserted DNA fragment was used as a probe for the Southern blot hybridization of the remaining 12 clones according to the standard method. As the result, the inserted DNA fragments of nine clones (Lambda gt11 CENP-3, 5, 6, 8, 9, 10, 11, 12 and 13) were found to be hybridized with the probe. The same procedure was repeated for the remaining three clones using an inserted DNA fragment derived from one clone (i.e., Lambda gt11 CENP-2) among the remaining three clones as the probe. As the result, the remaining two clones (Lambda gt11 CENP-4 and 7) were hybridized with the probe. From these experiments, it was found that the 13 clones can be divided into two groups; A (Lambda gt11 CENP-1, 3, 5, 6, 8, 9, 10, 11, 12 and 13) and B (Lambda gt11 CENP-2, 4 and 7).

The inserted DNA fragments of these groups were digested with various restriction enzymes, and the cleaved DNA fragments were subjected to agarose gel electrophoresis for size determination to obtain the restriction maps. The inserted DNA fragments of the A group were found to belong to the same group of CENP-B gene which had been cloned previously by Earnshaw, et al. [Earnshaw, W. C., et al., *J. Cell Biol.*, 104: 817 (1987)], while the restriction maps of the inserted DNA fragments of the B group did not correspond to the CENP-B gene of Earnshaw et al. and was thought to code other human centromere antigen. The restriction map of the clone which contains the longest DNA insert in the A group is shown in FIG. 1. The unit of figures in parentheses in FIG. 1 is kb. The arrow indicates the orientation of the reading frame of the gene.

The DNA inserts of the ten clones belonging to the A group which are assumed to contain CENP-B gene were recloned into a EcoRI-NotI site of a plasmid vector pGEMEX-12, each of which was designated as pCENP-B-1, 3, 5, 6, 8, 9, 10, 11, 12 and 13, respectively. A plasmid vector pGEMEX TM -1 manufactured by Promega Co. was used to prepare pGEMEX-12, and the vector pGEMEX-12 was prepared by double-digestion with restriction enzymes SfiI and SacI, then the 3' overhang removed by Klenow fragment followed by ligation. By this procedure, the SfiI and SacI cleavage sites present in the multicloning site of pGEMEX TM -1 were removed. *E. coli* BL21 (DE3) transformed with each of these plasmids pCENP-B-1, 3, 5, 6, 8, 9, 10, 11, 12 and 13 were cultured individually under the presence of IPTG, and ten species of CENP-B antigen polypeptides were obtained. All of the DNA inserts recloned in pGEMEX-12 are in frame of T7 gene 10, and the produced CENP-B antigen polypeptides are fusion proteins with T7 gene 10 protein. The CENP-B antigen polypeptides obtained were assayed by Western blot [Towbin, H., et al., *Proc. Natl. Acad. USA.*, 76: 4350 (1979)] using 40 patient sera diagnosed as positive for anti-centromere antibody and four sera from healthy individuals diagnosed as negative for anti-centromere antibody by indirect immunofluorescence. As the result, these ten species of CENP-B antigen polypeptides were positive for all the 40 patient sera and negative for all the four sera from healthy individuals.

Consequently, pCENP-B-1 containing the shortest DNA insert among these ten clones was used for analysis of the epitope of CENP-B antigen. The restriction map of the clone containing the longest inserted DNA fragment and the restriction map of the inserted DNA fragment of pCENP-B-1 are shown in FIG. 2. The orientation of the reading frame is in the direction from left to right in FIG. 2.

Figure 3A:
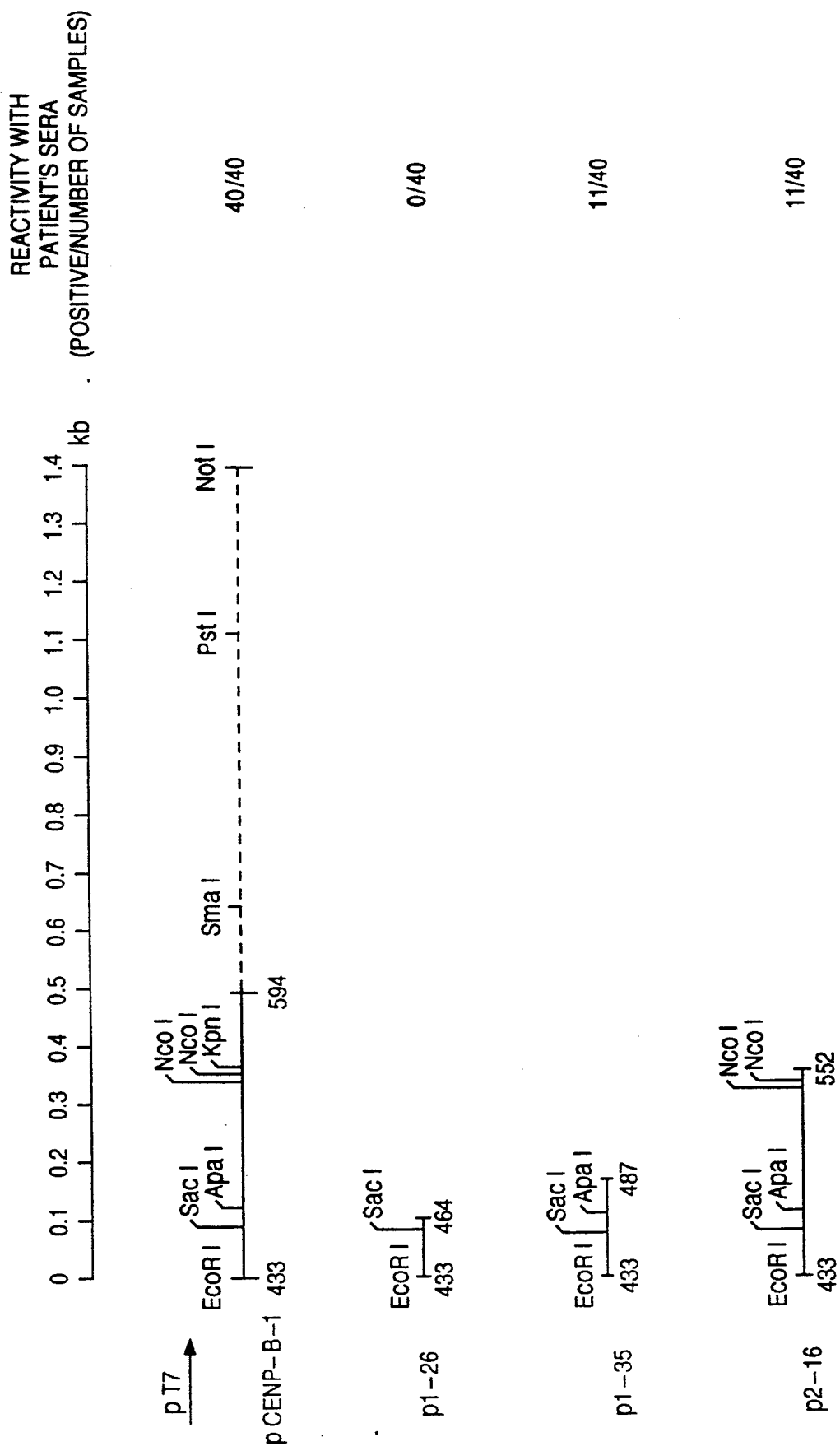
FIGS. 3a and b show the inserted fragments of deletion mutant plasmids in which a deletion mutation has been introduced in one direction of pCENP-B-1. The names of each plasmid are shown at the left end and the reactivities of the polypeptides coded by the plasmids with anti-centromere antibody-positive patient sera (40 serum samples) examined by Western blot are shown at the right end.
Figure 3B:
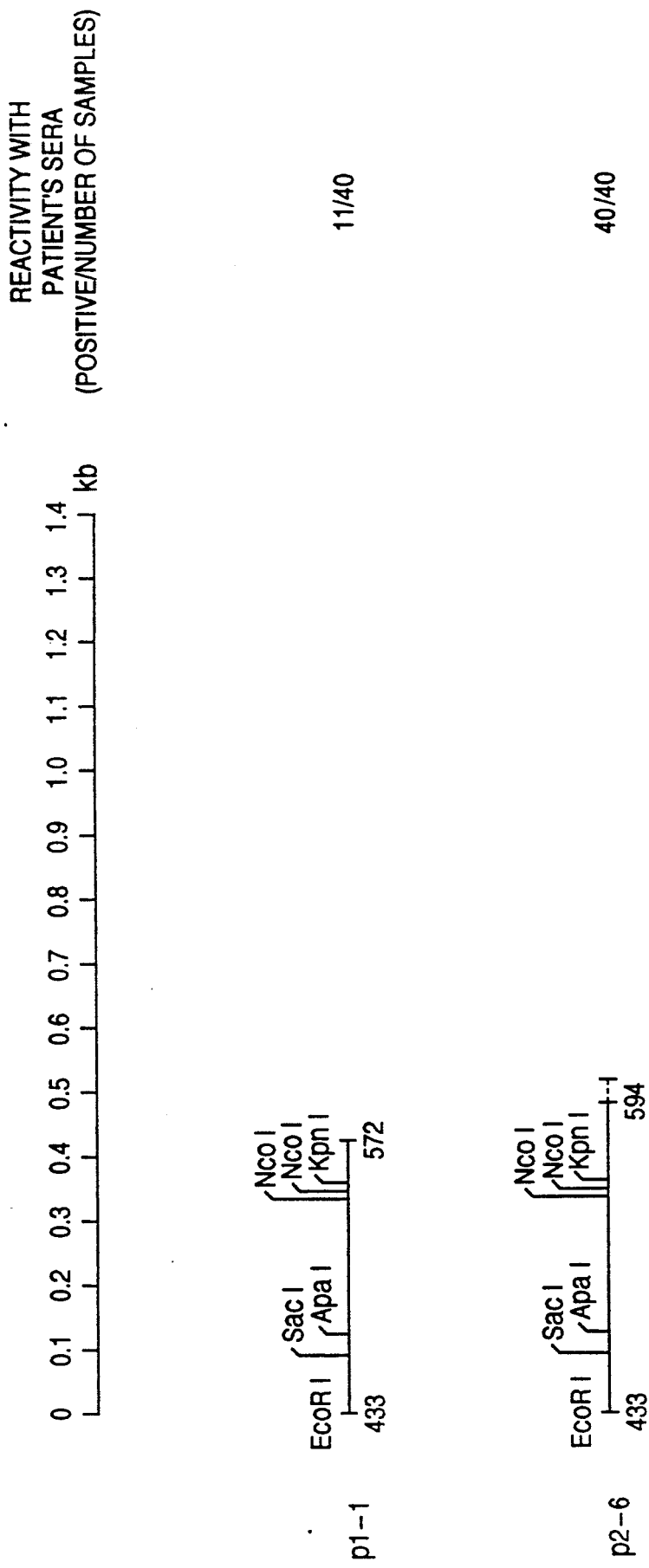

5. Preparations of a Mutant Plasmid Having a Deletion at 3' End and a Polypeptide Having a Deletion at the Carboxyl Terminus Using the Mutant Plasmid A mutant plasmid of pCENP-B-1 with a deletion at 3' end of CENP-B gene, i.e. with a deletion from the NotI site in FIG. 2 was prepared using a Deletion Kit manufactured by Nippon Gene Co. Firstly, pCENP-B-1 was cleaved with restriction enzymes NotI and EcoT22I followed by being reacted with *E. coli* exonuclease III to obtain a double-stranded DNA having the deletion in one direction. Preparation of a plasmid with an introduced deletion in one direction utilizing exonuclease III is described in detail in "Zoku Seikagaku Jikken Kouza, Vol. 1, 'Methods for Studying Genes II', The Japanese Biochemical Society ed., pp. 289–305". *E. coli* JM109 was transformed with each of the deletion mutant plasmids having the deletion in one direction obtained as described above to prepare plasmid clones with the deletion in one direction. A double-stranded DNA was prepared from each of the plasmid clones, and the extent of the deletion was analyzed by the restriction enzyme cleavage pattern, and then DNAs were prepared from suitable clones, pl-26, pl-35, p2-16, pl-1 and p2-6 (the restriction maps of these clones are shown in FIG. 3). *E. coli* BL 21 (DE 3) was transformed with each of the DNAs and cultured in the presence of IPTG to obtain each of the polypeptides (a fusion protein of the polypeptide coded by each of the deletion mutant plasmids fused with T7 gene 10 protein). The reactivity of each of the polypeptides with the 40 patient sera positive for anti-centromere antibody used in item 4 above, was analyzed by Western blot using each of the polypeptides as the antigen. This method was also employed in the examples below for examining the reactivity with the sera. The results with each of the corresponding deletion mutant plasmids are shown in FIG. 3. The solid lines represent translated regions and the dashed lines represent non-translated regions in FIG. 3. The numbers shown on the scale at the top of the figure represent the numbers of nucleotides (kb), and the numbers below each of the restriction map represent the amino acid sequence number. The amino acid sequence number corresponds to those described in the literature by Earnshaw, et al. (supra). The above-mentioned definitions can be applied in FIGS. 5 and 6 described below. According to the results, the CENP-B antigen polypeptide coded by pCENP-B-1 contains a plurality of epitopes. At least one epitope is contained in a portion up to the amino acid No. 487 and another epitope is contained in a portion up to the amino acid No. 594.

Determination of Polynucleotide Sequence

Using each of the deletion mutant plasmids (see FIG. 3) obtained in section 5 as a template, the nucleotide sequence of each of the DNA fragments was determined by the dideoxynucleotide method [Sanger, F., et al., *Proc. Natl. Acad. Sci. USA.*, 74: 5463 (1977)] using a SP6 primer (Promega Co.) and Sequenase TM (U.S. Biochemicals Co.). Furthermore, the complete nucleotide sequence of the coding region of CENP-B gene (the short fragment at 5' end shown in FIG. 2) inserted in pCENP-B-1 was determined by each of the nucleotides sequence of the DNA fragments. The complete nucleotide sequence and the deduced amino acid sequence are shown in SEQ ID NO:3 in Sequence Listing and in FIG. 4. Both amino acid numbers in FIGS. 3 and 4 were numbered corresponding to those in the literature by Eranshaw et al. (supra). As the result, three nucleotides were different between the data of Earnshaw et al. and our data, and so were the amino acids corresponding to each of the nucleotides, which are underlined in FIG. 4. The corresponding amino acids are replaced with ATG(Met) for AGG(Arg), with CTT(Leu) for GTT(Val),and with CTA(Leu) for CGA(Arg) in the data by Earnshaw et al.

7. Identification of the Epitope (Epitope II) Coded Within pCENP-B-1

Figure 5:
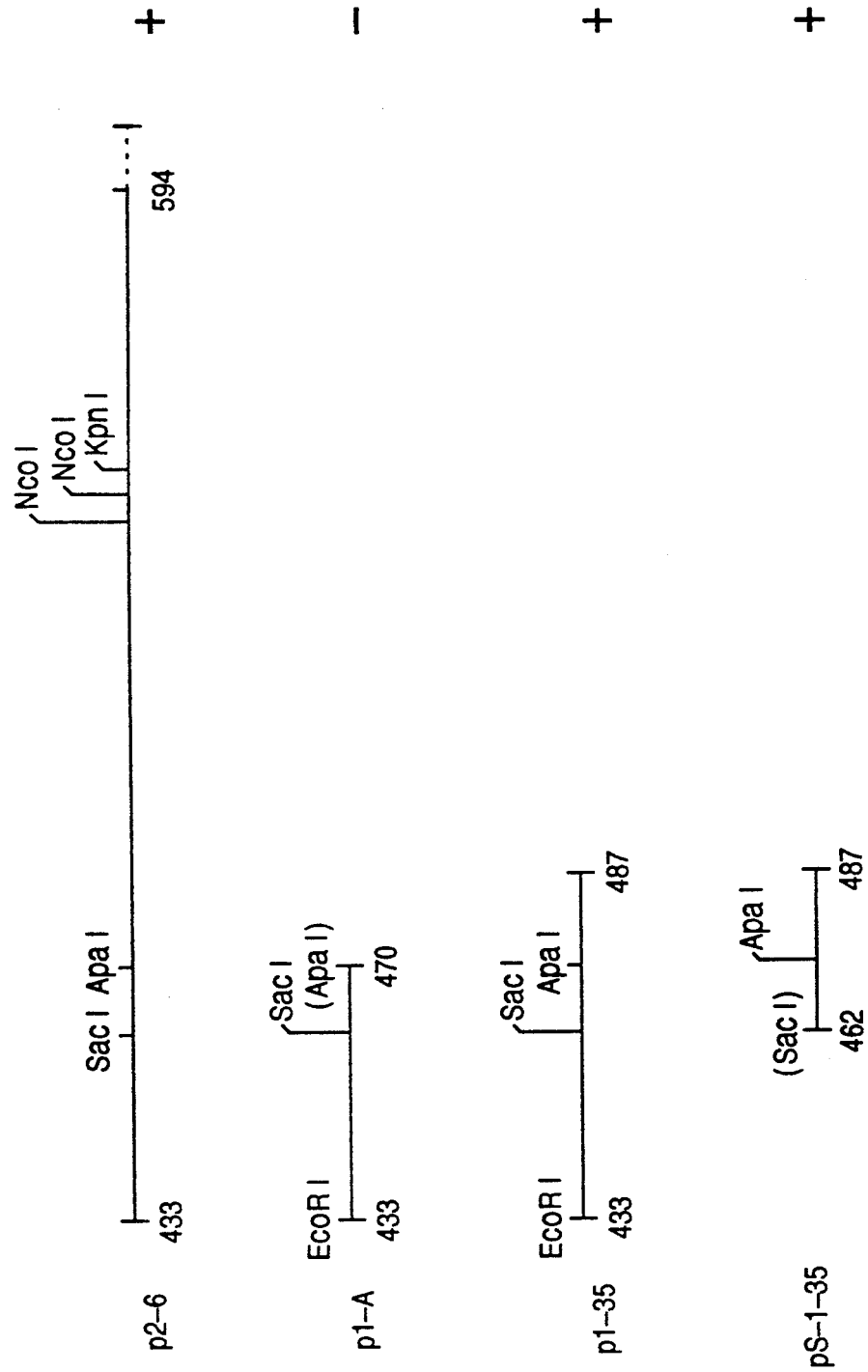
FIG. 5 illustrates the insert fragments of the deletion mutant plasmids derived from pCENP-B-1, which indicates that the region of the fragment contained in pS-1-35 is the minimum region of the epitope II. The reactivities of the polypeptides coded by the plasmids with the group II patient sera are shown at the right end.

The analysis for the epitope II was performed using patient sera positive for both of the polypeptides coded within pl-35 and p2-6, the sera are referred to as group II below, among the deletion mutant plasmids pl-26, pl-35, p2-16, pl-1 and p2-6 (see FIG. 3) obtained in section 5. Firstly, pCENP-B-1 was cleaved with restriction enzymes ApaI and NotI followed by the treatment with Klenow fragment to make blunt ends, then religated to prepare a plasmid pl-A in which the ApaI-NotI fragment was deleted. The fragment contained in the plasmid is shown in FIG. 5. The polypeptide coded by pl-A did not react with group II patient sera. Next, pl-35 described in section 5 was cleaved with restriction enzymes EcoRI and SacI followed by the treatment with Klenow fragment to make blunt ends, then religated to prepare a plasmid pS-1-35 in which the EcoRI-SacI fragment was deleted. The fragment contained in the plasmid was shown in FIG. 5. This fragment is in frame of T7 gene 10. The polypeptide obtained from this plasmid reacted with group II patient sera. The fragments contained in each of the plasmids and the reactivities of the polypeptides obtained from the plasmids are shown in FIG. 5. In the section for reactivity, (+) represents for positive and (−) for negative in FIG. 5. The restriction sites shown in parentheses are absent because of the treatment with a Klenow fragment in FIG. 5, and also in FIG. 6. The solid lines represent coding regions and the dashed lines represent non-coding regions.

According to the results described above, epitope II recognized by group II patient sera was identified as the polypeptide contained in the 26 amino acid sequence of 462 to 487.

8. Identification of the Epitope (Epitope I) Coded Within pCENP-B-1

The analysis for the epitope I region was performed as follows using the positive patient sera (group I) which reacted only with the polypeptide coded by p2-6 (see FIG. 3) shown in section 5.

Figure 6A:
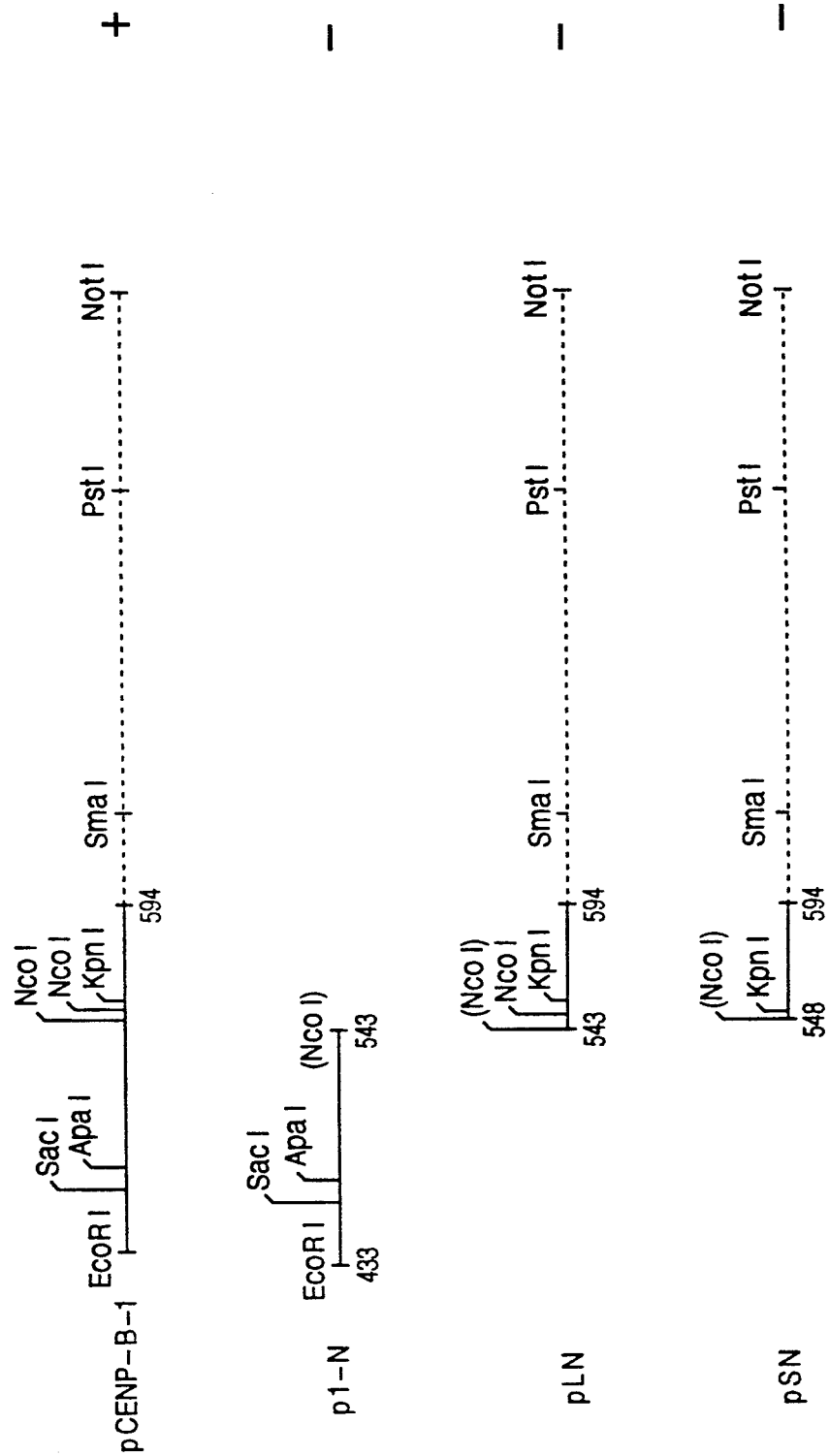
FIGS. 6a and b illustrate the insert fragments of the deletion mutant plasmids derived from pCENP-B-1, which indicates that the region of the fragment contained in pB-2-6 is the minimum region of the epitope I. The reactivities of the polypeptides coded by the plasmids with the group I patient sera are shown at the right end.

Firstly, pCENP-B-1 was double-digested with NcoI and NotI followed by the treatment with Klenow fragment to make blunt ends, then religated to prepare a plasmid p1-N in which the NcoI-NotI fragment was deleted from pCENP-B-1. The fragment contained in the plasmid is shown in FIG. 6.

Next, about 1.3 kb EcoRI-NotI fragment obtained by EcoRI/NotI double digestion of pCENP-B-1 was recloned into the EcoRI-NotI site of the plasmid vector pGEMEX TM -1 (Promega Co.) followed by the cleavage with EcoRI, then partially digested with NcoI. The fragment was treated with a Klenow fragment to make all the ends blunt, then religated to prepare two species of deletion mutant plasmid, pLN and pSN. The DNA fragments contained in pLN and pSN are shown in FIG. 6. All of pl-N, pLN, and pSN are in frame of T7 gene 10. The polypeptides coded in these deletion mutant plasmids did not react with the above-mentioned group I patient sera.

Accordingly, polypeptides with extension from the amino terminus of the polypeptide coded in pLN were examined. The double-stranded DNA fragment I shown in FIG. 7 was prepared by synthesizing each of the strands of the DNA in an automated DNA synthesizer manufactured by Pharmacia, then annealing both strands. This DNA fragment encodes the amino acid sequence from Asp at 530 (98 in SEQ ID NO:3) to Met at 548 (116 in SEQ ID NO:3), to the amino terminus of which an EcoRI cleavage site is added and to the carboxyl terminus of which is altered to contain a NcoI cleavage site. The following deletion mutant plasmids were prepared using this DNA fragment. After the double-digestion of p2-6 (see FIG. 3) described in section 5 with EcoRI and NcoI, the DNA fragment was inserted and religated to prepare pB-2-6. Similarly, pB-1-1 was prepared by inserting DNA fragment I from EcoRI/NcoI double-digested pl-1, and pB-2-16 was prepared by inserting DNA fragment I from EcoRI/NcoI double-digested p2-16. The DNA fragments contained in pB-2-6, pB-1-1 and pB-2-16 are shown in FIG. 6. All these fragments are in frame of T7 gene 10. The polypeptide coded by pB-2-6 reacted with the above-mentioned group I patient sera, while the peptides coded by pB-1-1 or pB-2-16 did not. These results are shown in FIG. 6.

According to these results, the epitope recognized by the group I patient sera (epitope I) was identified as the polypeptide which is present within a 65 amino acid sequence from 530 to 594. There are amino acid differences at three sites in total in the epitope I from the data of Earnshaw et al. as described in the section 6.

EXAMPLE II

Each of *E. coli* BL 21 (DE 3) transformed with the plasmid pS-1-35 obtained in section 7 of Example I and with the plasmid pB-2-6 obtained in section 8 of Example I respectively was cultured in the presence of IPTG. By using each of the fusion proteins of the obtained polypeptides fused with T7 gene 10 protein as the antigen, which contains the epitope I and the epitope II respectively, the reactivities of the polypeptides with the 40 patient sera diagnosed as positive for anti-centromere antibody and the four sera from healthy individuals diagnosed as negative by immunofluorescence were assayed on Western blot. The results are shown in TABLE 1.

TABLE 1

| CENP-B | antigen polypeptides | Serum sample (positive/number of samples) | |
|---|---|---|---|
| | | healthy | patient |
| pB-2-6 | derived polypeptide (epitope I) | 0/4 | 40/40 |
| pS-1-35 | derived polypeptide (epitope II) | 0/4 | 11/40 |

According to the present invention, epitope regions of human centromere protein B are elucidated, and polypeptides containing the epitope are provided. The polypeptides can be produced in a large quantity by chemical synthesis, by an enzymatic method, and by genetic engineering. By using the obtained polypeptides, it is possible to detect human anti-centromere antibody readily and precisely. Furthermore, determinations using the polypeptides containing each epitope allow a precise classification of disease type of a patient having human anti-centromere antibody.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

---

What is claimed is:

1. A polypeptide containing an epitope of human centrometer protein B, wherein the polypeptide is selected from the group consisting of polypeptide I and polypeptide II having the following amino acid sequences shown by SEQ ID No:1 and SEQ ID No:2;

Polypeptide I:
Asp Gly Asp Glu Val Pro Val Pro Ser Phe Gly Glu Ala Met
Ala Tyr Phe Ala Met Val Lys Arg Tyr Leu Thr Ser Phe Pro
Ile Asp Asp Arg Val Gln Ser His Ile Leu His Leu Glu His
Asp Leu Val His Val Thr Arg Lys Asn His Ala Arg Gln Ala
Gly Val Arg Gly Leu Gly His Gln Ser Polypeptide II:
Ser Ser Glu Gly Leu Glu Ala Glu Asp Trp Ala Gln Gly Val
Val Glu Ala Gly Gly Ser Phe Gly Ala Tyr Gly Ala 2. A method for detecting a human anti-centromere antibody comprising the steps of:
(a) adding the polypeptide according to claim 1 to a sample to contact the polypeptide with a human anti-centromere antibody contained in the sample; and
(b) detecting the human anti-centromere antibody bound to the polypeptide.

* * * * *

UNITED STATES PATENT AND TRADEMARK OFFICE
CERTIFICATE OF CORRECTION

PATENT NO. : 5,296,383
DATED : March 22, 1994
INVENTOR(S) : M. Himeno et al.

It is certified that error appears in the above-indentified patent and that said Letters Patent is hereby corrected as shown below:

The drawings sheet consisting of Fig. 1 should be deleted and replaced with the drawing sheet consisting of Fig. 1 as shown on the attached page.

The drawings sheet consisting of Fig. 4A should be deleted and replaced with the drawings sheet consisting of Fig. 4A as shown on the attached page.

The drawings sheet consisting of Fig. 4B should be deleted and replaced with the drawing sheet consisting of Fig. 4B as shown on the attached page.

Signed and Sealed this

Sixth Day of September, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,296,383  
DATED : March 22, 1994  
INVENTOR(S) : M. Himeno et al.

Page 2 of 4

It is certified that error appears in the above-indentified patent and that said Letters Patent is hereby corrected as shown below:

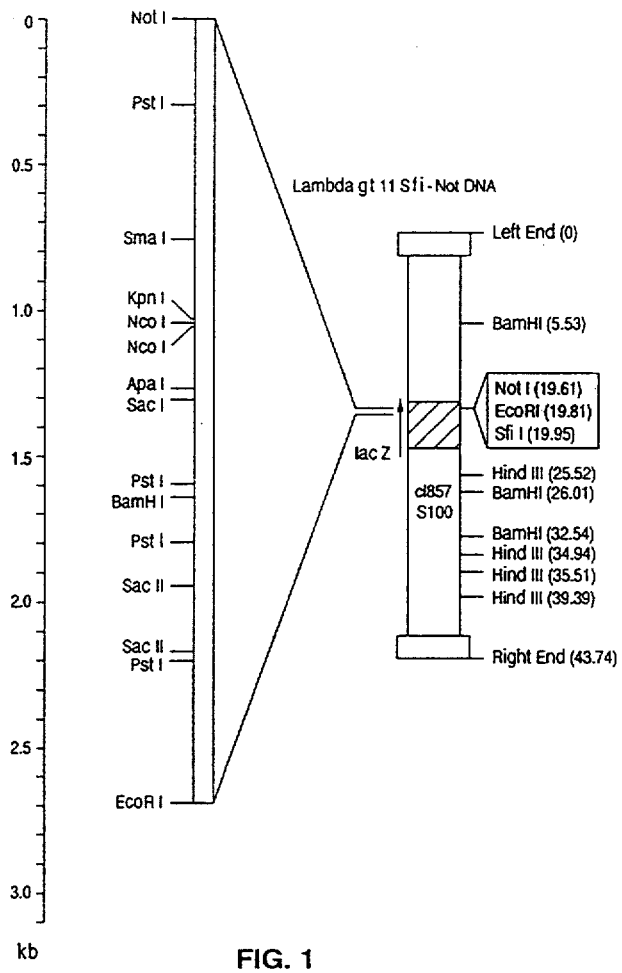

FIG. 1

UNITED STATES PATENT AND TRADEMARK OFFICE
CERTIFICATE OF CORRECTION

PATENT NO. : 5,296,383  Page 3 of 4
DATED : March 22, 1994
INVENTOR(S) : M. Himeno et al.

It is certified that error appears in the above-identified patent and that said Letters Patent is hereby corrected as shown below:

```
433                       440                                      450
GAA GGA GAG GAA TTG GGG GAG GAA GAG GAG GTG GAG GAG GAG GGT GAT GTT GAT AGT GAT
Glu Gly Glu Glu Leu Gly Glu Glu Glu Glu Val Glu Glu Glu Gly Asp Val Asp Ser Asp 460                                      470
GAA GAA GAG GAG GAA GAT GAG GAG AGC TCC TCG GAG GGC TTG GAG GCT GAG GAC TGG GCC
Glu Glu Glu Glu Glu Asp Glu Glu Ser Ser Ser Glu Gly Leu Glu Ala Glu Asp Trp Ala 480                                      490
CAG GGA GTA GTG GAG GCC GGT GGC AGC TTC GGG GCT TAT GGT GCC CAG GAG GAA GCC CAG
Gln Gly Val Val Glu Ala Gly Gly Ser Phe Gly Ala Tyr Gly Ala Gln Glu Glu Ala Gln 500                                      510
TGC CCT ACT CTG CAT TTC CTG GAA GGT GGG GAG GAC TCT GAT TCA GAC AGT GAG GAA GAG
Cys Pro Thr Leu His Phe Leu Glu Gly Gly Glu Asp Ser Asp Ser Asp Ser Glu Glu Glu
```

FIG. 4A

UNITED STATES PATENT AND TRADEMARK OFFICE
CERTIFICATE OF CORRECTION

PATENT NO. : 5,296,383  
DATED : March 22, 1994  
INVENTOR(S) : M. Himeno et al.

Page 4 of 4

It is certified that error appears in the above-indentified patent and that said Letters Patent is hereby corrected as shown below:

```
                  520                                              530
GAC GAT GAG GAA GAG GAT GAT GAA GAT GAA GAC GAC GAT GAT GAT GAG GAG GAT GGT GAT
Asp Asp Glu Glu Glu Asp Asp Glu Asp Glu Asp Asp Asp Asp Asp Glu Glu Asp Gly Asp 540                                              550
GAG GTG CCT GTA CCC AGC TTT GGG GAG GCC ATG GCT TAC TTT GCC ATG GTC AAG AGG TAC
Glu Val Pro Val Pro Ser Phe Gly Glu Ala Met Ala Tyr Phe Ala Met Val Lys Arg Tyr 560                                              570
CTG ACC TCC TTC CCC ATT GAT GAC CGC GTG CAG AGC CAC ATC CTC CAC TTG GAA CAC GAT
Leu Thr Ser Phe Pro Ile Asp Asp Arg Val Gln Ser His Ile Leu His Leu Glu His Asp 580                                              590
CTG GTT CAT GTG ACC AGG AAG AAC CAC GCC AGG CAG GCG GGA GTT CGA GGT CTT GGA CAT
Leu Val His Val Thr Arg Lys Asn His Ala Arg Gln Ala Gly Val Arg Gly Leu Gly His

594
CAA AGC TGA
Gln Ser
```

FIG. 4B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( v ) FRAGMENT TYPE: internal fragment ( v i ) ORIGINAL SOURCE:
        ( A ) ORGANISM: human ( x i ) SEQUENCE DESCRIPTION: SEQ ID NO:1:

```
Asp Gly Asp Glu Val Pro Val Pro Ser Phe Gly Glu Ala Met Ala Tyr
 1               5                  10                  15
Phe Ala Met Val Lys Arg Tyr Leu Thr Ser Phe Pro Ile Asp Asp Arg
                20                  25                  30
Val Gln Ser His Ile Leu His Leu Glu His Asp Leu Val His Val Thr
                35                  40                  45
Arg Lys Asn His Ala Arg Gln Ala Gly Val Arg Gly Leu Gly His Gln
        50                  55                  60
Ser
65
```

( 2 ) INFORMATION FOR SEQ ID NO:2:

( i ) SEQUENCE CHARACTERISTICS:
        ( A ) LENGTH: 26 amino acids (B) TYPE: amino acid
(D) TOPOLOGY: linear (ii) MOLECULE TYPE: peptide (v) FRAGMENT TYPE: internal fragment (vi) ORIGINAL SOURCE:
(A) ORGANISM: human (xi) SEQUENCE DESCRIPTION: SEQ ID NO:2:

| Ser | Ser | Glu | Gly | Leu | Glu | Ala | Glu | Asp | Trp | Ala | Gln | Gly | Val | Val | Glu |
|---|---|---|---|---|---|---|---|---|---|---|---|---|---|---|---|
| 1 | | | | 5 | | | | | 10 | | | | | 15 | |

| Ala | Gly | Gly | Ser | Phe | Gly | Ala | Tyr | Gly | Ala |
|---|---|---|---|---|---|---|---|---|---|
| | | | 20 | | | | | 25 | 26 |

(2) INFORMATION FOR SEQ ID NO:3:

(i) SEQUENCE CHARACTERISTICS:
(A) LENGTH: 489 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: human (ix) FEATURE:
(A) NAME/KEY: CDS
(B) LOCATION: 1 to 489
(C) IDENTIFICATION METHOD: by experiment (xi) SEQUENCE DESCRIPTION: SEQ ID NO:3:

```
GAA GGA GAG GAA TTG GGG GAG GAA GAG GAG GTG GAG GAG GAG GGT GAT        48
Glu Gly Glu Glu Leu Gly Glu Glu Glu Glu Val Glu Glu Glu Gly Asp
 1           5                   10                  15

GTT GAT AGT GAT GAA GAA GAG GAG GAA GAT GAG GAG AGC TCC TCG GAG        96
Val Asp Ser Asp Glu Glu Glu Glu Glu Asp Glu Glu Ser Ser Ser Glu
            20                  25                  30

GGC TTG GAG GCT GAG GAC TGG GCC CAG GGA GTA GTG GAG GCC GGT GGC       144
Gly Leu Glu Ala Glu Asp Trp Ala Gln Gly Val Val Glu Ala Gly Gly
        35                  40                  45

AGC TTC GGG GCT TAT GGT GCC CAG GAG GAA GCC CAG TGC CCT ACT CTG       192
Ser Phe Gly Ala Tyr Gly Ala Gln Glu Glu Ala Gln Cys Pro Thr Leu
    50                  55                  60

CAT TTC CTG GAA GGT GGG GAG GAC TCT GAT TCA GAC AGT GAG GAA GAG       240
His Phe Leu Glu Gly Gly Glu Asp Ser Asp Ser Asp Ser Glu Glu Glu
65                  70                  75                  80

GAC GAT GAG GAA GAG GAT GAT GAA GAT GAA GAC GAC GAT GAT GAT GAG       288
Asp Asp Glu Glu Glu Asp Asp Glu Asp Glu Asp Asp Asp Asp Asp Glu
                85                  90                  95

GAG GAT GGT GAT GAG GTG CCT GTA CCC AGC TTT GGG GAG GCC ATG GCT       336
Glu Asp Gly Asp Glu Val Pro Val Pro Ser Phe Gly Glu Ala Met Ala
            100                 105                 110

TAC TTT GCC ATG GTC AAG AGG TAC CTG ACC TCC TTC CCC ATT GAT GAC       384
Tyr Phe Ala Met Val Lys Arg Tyr Leu Thr Ser Phe Pro Ile Asp Asp
        115                 120                 125

CGC GTG CAG AGC CAC ATC CTC CAC TTG GAA CAC GAT CTG GTT CAT GTG       432
Arg Val Gln Ser His Ile Leu His Leu Glu His Asp Leu Val His Val
    130                 135                 140

ACC AGG AAG AAC CAC GCC AGG CAG GCG GGA GTT CGA GGT CTT GGA CAT       480
Thr Arg Lys Asn His Ala Arg Gln Ala Gly Val Arg Gly Leu Gly His
145                 150                 155                 160

CAA AGC TGA                                                            489
Gln Ser
162
```

(2) INFORMATION FOR SEQ ID NO:4:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Gly Glu Glu Leu Gly Glu Glu Glu Glu Val Glu Glu Glu Gly Asp
 1               5                  10                  15
Val Asp Ser Asp Glu Glu Glu Glu Glu Asp Glu Glu Ser Ser Ser Glu
            20                  25                  30
Gly Leu Glu Ala Glu Asp Trp Ala Gln Gly Val Val Glu Ala Gly Gly
             35              40                  45
Ser Phe Gly Ala Tyr Gly Ala Gln Glu Glu Ala Gln Cys Pro Thr Leu
         50              55                  60
His Phe Leu Glu Gly Gly Glu Asp Ser Asp Ser Asp Ser Glu Glu Glu
 65              70                  75                  80
Asp Asp Glu Glu Glu Asp Asp Glu Asp Glu Asp Asp Asp Asp Asp Glu
                 85              90                  95
Glu Asp Gly Asp Glu Val Pro Val Pro Ser Phe Gly Glu Ala Met Ala
            100             105                 110
Tyr Phe Ala Met Val Lys Arg Tyr Leu Thr Ser Phe Pro Ile Asp Asp
         115             120                 125
Arg Val Gln Ser His Ile Leu His Leu Glu His Asp Leu Val His Val
    130             135             140
Thr Arg Lys Asn His Ala Arg Gln Ala Gly Val Arg Gly Leu Gly His
145             150                 155                 160
Gln Ser
```